(12) United States Patent
Kihara

(10) Patent No.: US 6,921,375 B2
(45) Date of Patent: Jul. 26, 2005

(54) LUMBAR SUPPORTER

(75) Inventor: Shunichi Kihara, 2-47-31, Motomiya, Otsu-shi, Shiga-ken (JP)

(73) Assignees: Taketora Co., Ltd., Tokyo (JP); Shunichi Kihara, Otsu (JP)

( * ) Notice: Subject to any disclaimer, the term of this patent is extended or adjusted under 35 U.S.C. 154(b) by 7 days.

(21) Appl. No.: 10/656,225

(22) Filed: Sep. 8, 2003

(65) Prior Publication Data

US 2004/0132380 A1 Jul. 8, 2004

(30) Foreign Application Priority Data

Jan. 7, 2003 (JP) ........................................ 2003-000768

(51) Int. Cl.[7] .............................. A61F 5/00; A61F 5/02; A41F 9/00; A41D 13/00; A41D 27/26
(52) U.S. Cl. ..................... 602/5; 602/19; 2/44; 2/311; 2/322; 2/467
(58) Field of Search ................................ 128/874, 845, 128/846; 602/13, 19, 5, 345; 2/467, 44, 311, 315, 321, 322

(56) References Cited

U.S. PATENT DOCUMENTS

| | | | | |
|---|---|---|---|---|
| 3,116,736 A | * | 1/1964 | Alberts | 450/100 |
| 4,498,201 A | * | 2/1985 | Carter | 2/312 |
| 5,122,111 A | * | 6/1992 | Sebastian et al. | 602/19 |
| 5,207,636 A | * | 5/1993 | Striano | 602/19 |
| 5,421,809 A | * | 6/1995 | Rise | 602/19 |
| 5,591,122 A | * | 1/1997 | Yewer, Jr. | 602/19 |
| 5,690,122 A | * | 11/1997 | Weber-Unger | 128/876 |
| 5,913,410 A | * | 6/1999 | Tsuchiya | 2/311 |
| 5,950,628 A | * | 9/1999 | Dunfee | 128/874 |
| 6,066,108 A | * | 5/2000 | Lundberg | 602/23 |
| 6,146,345 A | * | 11/2000 | Mignard | 602/19 |

FOREIGN PATENT DOCUMENTS

JP     2002095686 A  *  4/2002

* cited by examiner

Primary Examiner—Henry Bennett
Assistant Examiner—Dinnatia Doster-Greene
(74) Attorney, Agent, or Firm—Manabu Kanesaka

(57) ABSTRACT

A lumbar fixed belt that mainly holds a lumbar and a pelvic fixed belt that mainly holds the pelvis are integrally provided, and the pelvic fixed belt is inclined to the lumbar fixed belt 2 at 20° to 30° toward a lumboabdominal region, correspondingly to a physiological pelvic angle of inclination θ.

9 Claims, 4 Drawing Sheets

LUMBAR SUPPORTER

TECHNICAL FIELD

The present invention relates to a lumbar supporter for fixing a lumbar and its periphery in a normal posture, and more particularly to a lumbar supporter that can prevent displacement to an upper trunk after worn, while keeping a stable wearing posture.

BACKGROUND ART

Sufferers of lumbar region diseases such as lumbar distortion often wear a lumbar supporter around a lumbar in order to keep lumbar vertebrae in a normal posture. FIG. 5 shows an example thereof. A lumbar supporter 1 has a lumbar fixed belt 2 constituted by a band having enough length to be wrapped around a lumbar of a human body H.

The lumbar fixed belt 2 has a back support portion 21 in a center and belt portions 23a, 23b extending from both ends of the back support portion 21 sewn together via stretchable portions 22a, 22b.

A loop fastener 41 that forms one of engaging means 4 for holding the lumbar supporter 1 in a wrapped state is provided on an outer surface of each of the belt portions 23a, 23b. A hook fastener 42 that engages the loop fastener 41 is provided on a tip of an inner surface of either of the belt portions 23a, 23b (in this case, the belt portion 23b).

The lumbar supporter 1 also has an auxiliary belt 3 for ensuring tightening when worn. The auxiliary belt 3 has a pair of auxiliary flaps 31, 32 extending from both sides of the back support portion 21 along the loop fasteners 41. Hook fasteners 33, 34 that engage the loop fasteners 41, 41 are provided on inner surfaces of the auxiliary flaps 31, 32.

When the lumbar supporter 1 is used, the back support portion 21 is placed so that a longitudinal center thereof is substantially coaxial with a trunk axis L1 of the human body H, the both belt portions 23a, 23b are pulled around a lumboabdominal region, and wrapped around the human body H so that a longitudinal direction L2 of the belt portions 23a, 23b is perpendicular to the trunk axis L1, and then the hook fastener 42 of the belt portion 23b is engaged with the loop fastener 41 provided around the belt portion 23a.

After a supporter body is thus wrapped around the human body H, in order to ensure tightening in this case, the auxiliary flaps 31, 32 are pulled toward lumbar lateral sides, and the hook fasteners 33, 34 on both ends thereof are engaged with the loop fasteners 41, 41 of the belt portions 23a, 23b, thus ensuring tightening.

Wearing the lumbar supporter 1 offers the following advantages:

(1) A lumbodorsal region and a lumboabdominal region are tightened by the belt to increase intra-abdominal pressure and reduce weighted load on a spine or lumbar vertebrae.
(2) Wearing the lumbar supporter reminds a sufferer of his/her lumbar region disease to consciously restrict abrupt motion, forebend, or twisted motion.
(3) Muscular fatigue of other trunk muscles, caused by protecting a lumbar from pain, can be reduced.

However, the conventional lumbar supporter has the following problems to be solved:

[1] The human body is constricted from a lumbar toward an abdomen, and the supporter tends to be displaced to an upper trunk by motion such as walking.
[2] As a solution to [1], use of a wider belt is considered, but the wider belt also tightens the abdomen and is tight. Further, the abdomen is tightened to tighten a thorax, which relatively tends to loosen the tightening of the lumbar.
[3] The supporter does not fit a pelvis, and a lower edge of the supporter makes contact with an upper pelvis to cause pain or uncomfortable feeling, thus preventing sleep.
[4] For a protruding abdomen of an obese sufferer, lumbar vertebrae significantly warp and the abdomen protrudes, which makes it difficult to provide stable fixing and protection of the lumbar.
[5] The supporter has similar figures with emphasis on fixing and protection of the lumbar, and thus has a poor appearance when worn, and edges of the supporter protrude under a suit or a skirt, which may cause trouble in daily life.

SUMMARY OF THE INVENTION

The invention is achieved to solve the above described problems, and has an object to provide a lumbar supporter that can effectively prevent displacement to an upper trunk and integrally fix lumbar vertebrae and a pelvis, and further has a good appearance.

In order to achieve the object, the lumbar supporter according to the invention includes: a lumbar fixed belt constituted by a band, at least a part of which is a stretchable portion, and fitted from a lumbodorsal region toward a lumboabdominal region of a human body; and a pelvic fixed belt fitted substantially in parallel along a pelvic angle of inclination of the human body from the lumbodorsal region toward the lumboabdominal region.

Thus, two belts with different angles are wrapped around a lumbar, and one of the belts, the lumbar fixed belt, mainly tightens a lumbar and its periphery to increase intra-abdominal pressure, and the other of the belts, the pelvic fixed belt, mainly fixes a pelvis, thus effectively prevents displacement to an upper portion, while keeping a stable posture.

An angle of inclination of the pelvic fixed belt is preferably set to 20° to 30° forward toward the lumboabdominal region with respect to a trunk axis as a base axis.

The lumbar fixed belt and the pelvic fixed belt are sewn together at substantial centers thereof. Thus, the lumbar fixed belt that mainly protects the lumbar and the pelvic fixed belt that mainly protects the pelvis are coaxially and integrally formed to improve an appearance without loss of stability such as displacement.

For ensuring protection of the lumbodorsal region, the lumbar fixed belt preferably has a reinforcing plate placed along the lumbodorsal region. The reinforcing plate includes, for example, a piece of metal such as aluminum, or hard synthetic resin.

DETAILED DESCRIPTION

Figure 1A:
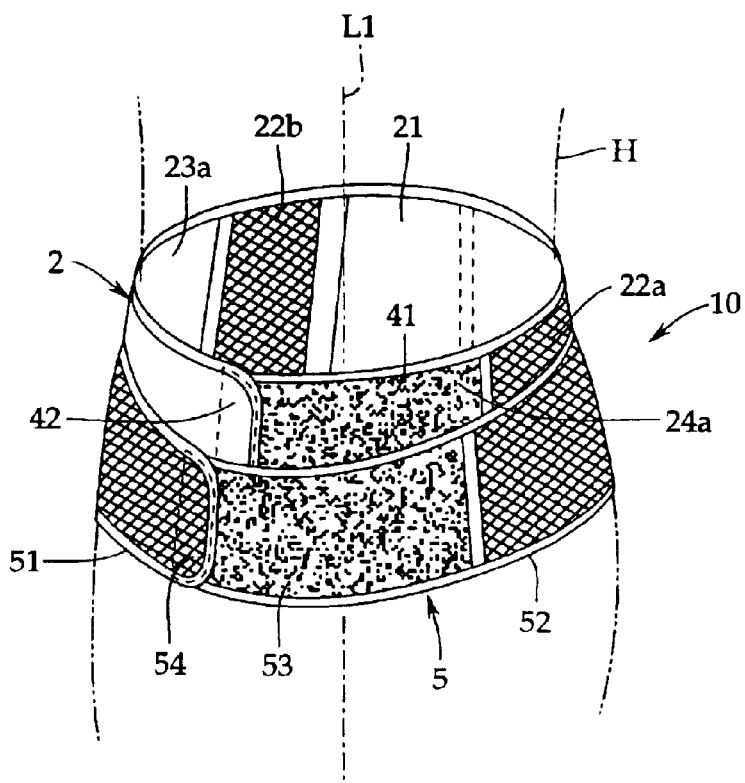
FIG. 1A shows a fitting state of a lumbar supporter according to an embodiment of the invention.
Figure 1B:
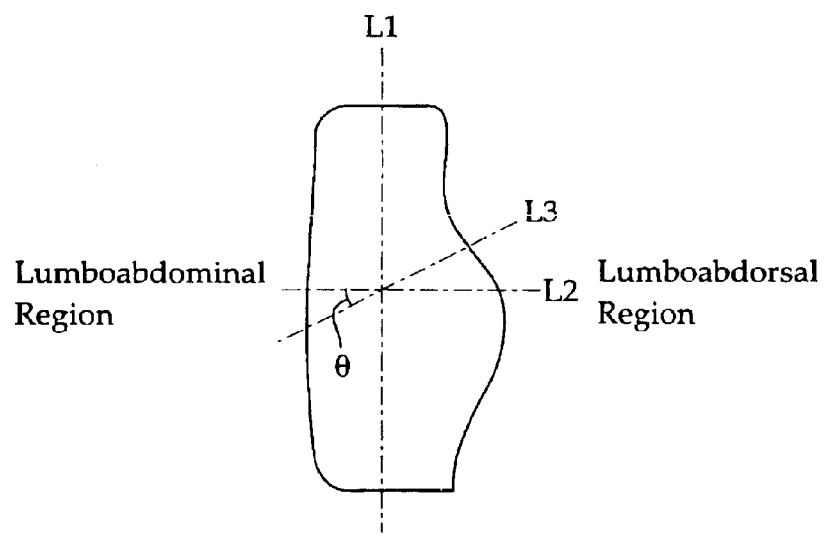
FIG. 1B is a perspective view of a relationship of axes of the lumbar supporter.
Figure 2:
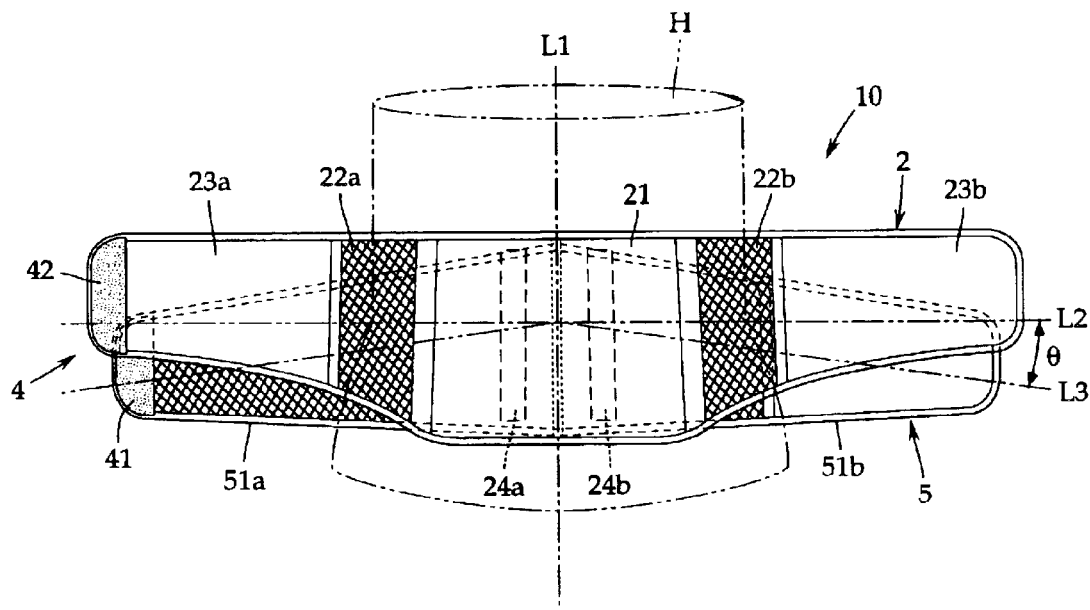
FIG. 2 is a back view of the lumbar supporter according to the embodiment, seen from a lumbodorsal side.
Figure 3:
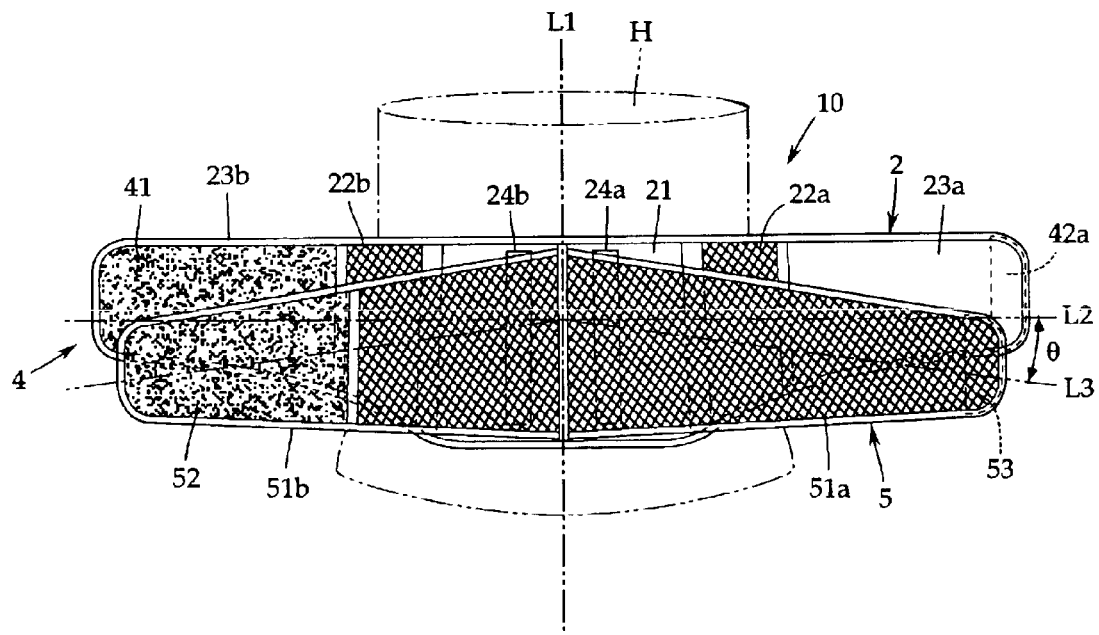
FIG. 3 is a front view of the lumbar supporter according to the embodiment, seen from a lumboabdominal side.
Figure 5:
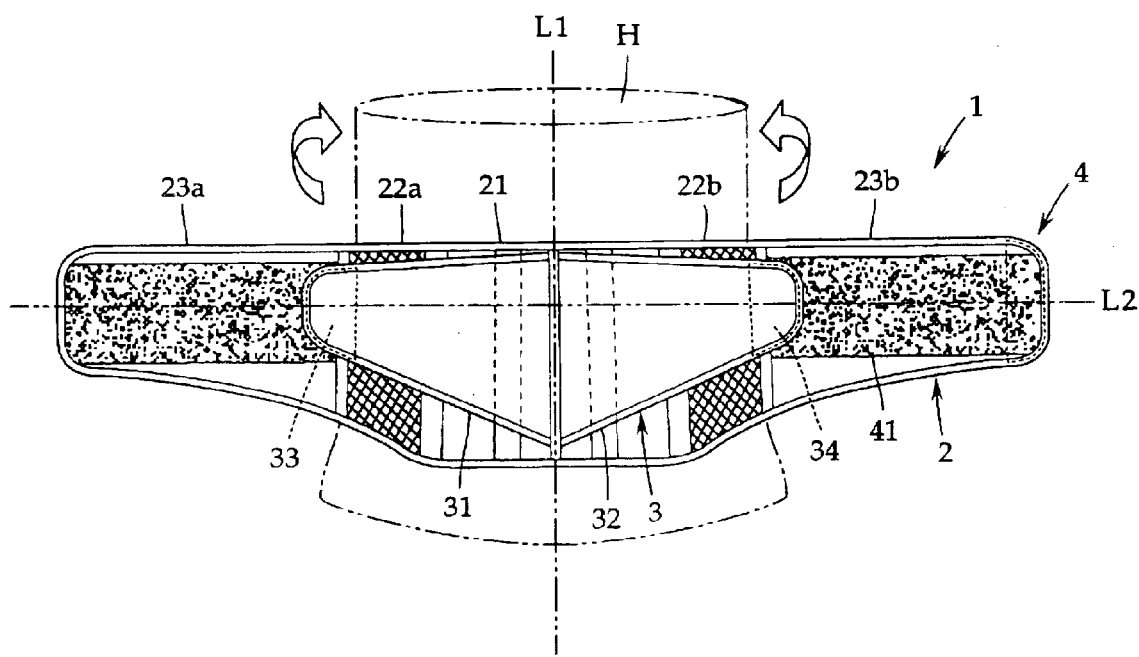
FIG. 5 is a back view of a conventional lumbar supporter, seen from a lumbodorsal side.

Now, an embodiment of the invention will be described below with reference to the drawings. FIGS. 1A and 1B shows a state of use of a lumbar supporter according to an embodiment of the invention, and schematically shows, in perspective, a relationship of axes of the lumbar supporter. FIG. 2 is a back view of the lumbar supporter (a lumbodorsal side), and FIG. 3 is a front view of the lumbar supporter (a lumboabdominal side). The same reference numerals denote the same components or similar components as in a conventional example shown in FIG. 5.

A lumbar supporter 10 includes a lumbar fixed belt 2 that mainly protects a lumbar, and a pelvic fixed belt 5 that mainly protects a pelvis, each of which is constituted by a band wrapped around the lumbar of a human body H.

As shown in FIG. 1B, the lumbar fixed belt 2 is wrapped from a lumbodorsal region (the right in FIG. 1B) toward a lumboabdominal region (the left in FIG. 1B) along an axis L2 (a longitudinal axis) perpendicular to a trunk axis L1, which is a base axis.

The pelvic fixed belt 5 is wrapped from the lumbodorsal region (the right in FIG. 1B) toward the lumboabdominal region (the left in FIG. 1B) substantially in parallel along an angle of inclination (a pelvic angle of inclination) of $\theta°$ forward with respect to the axis L2 of the lumbar fixed belt 2, with the trunk axis L1 as the base axis.

As shown in FIGS. 2 and 3, the lumbar fixed belt 2 has a back support portion 21 formed into a rectangle so as to cover the entire lumbodorsal region, stretchable portions 22a, 22b extending integrally from both ends of the back support portion 21, and belt portions 23a, 23b extending from free ends of the stretchable portions 22a, 22b.

The stretchable portions 22a, 22b and the belt portions 23a, 23b have lower edges curved toward upper edges, and thus the entire lumbar fixed belt 2 is formed so that a width thereof is gradually reduced from a center toward both ends.

In the embodiment, the back support portion 21 is made of an unstretchable cloth, and placed on the lumbodorsal region of the human body H. In the back support portion 21, a pair of reinforcing plates 24a, 24b formed by, for example, pieces of plate such as an aluminum plate are provided symmetrically with respect to the trunk axis L1, and the reinforcing plates 24a, 24b can keep the lumbar stretched. The back support portion 21 may be made of a stretchable cloth.

The stretchable portions 22a, 22b are made of a stretchable cloth, for example, with a mesh of rubber threads, and one end of each thereof is sewn to the back support portion 21, and the other ends thereof are sewn to the belt portions 23a, 23b.

In this embodiment, a mesh cloth having good breathability besides stretching properties is used for the stretchable portions 22a, 22b, but not limited to this, other stretchable materials can be appropriately selected.

The belt portions 23a, 23b are made of an unstretchable cloth like the back support portion 21, and as shown in FIG. 3, a loop fastener 41 that forms one of engaging means 4 is provided on an outer surface of the belt portion 23b (a surface in no contact with the human body H), and a hook fastener 42 that forms the other of the engaging means 4 is provided on a tip of an inner surface of the belt portion 23a (a surface in contact with the human body H).

In the embodiment, the loop fastener 41 and the hook fastener 42 are provided on one belt portion 23a, but may be provided on the other belt portion 23b. Further, a hook and loop fastener is used as the engaging means 4, but any means capable of fixing the belt can he appropriately selected.

The pelvic fixed belt 5 has a pair of pelvic belts 51a, 51b formed symmetrically with respect to the trunk axis L1 from the center of the back support portion 21 of the lumbar fixed belt 2, as shown in FIG. 3. Each of the pelvic belts 51a, 51b is provided so that an upper edge thereof (an axis L3) is inclined to the axis L2 perpendicular to the trunk axis L1 of the lumbar fixed belt 2, at $\theta°$ toward the lumboabdominal region.

The pelvic belts 51a, 51b are made of a cloth having, for example, stretchable properties with a mesh of rubber threads, like the stretchable portions 22a, 22b, and further having a low coefficient of friction. In the embodiment, a loop fastener 52 for engagement is uniformly formed on an outer surface of the pelvic belt 51b, and a hook fastener 53 that engages the loop fastener 52 is provided on a tip of an inner surface of the pelvic belt 51a.

In the embodiment, the angle of inclination $\theta$ of each of the pelvic belts 51a, 51b is set within 20° to 30°. The angle $\theta$ is an angle corresponding to an angle of physiological forward inclination of a pelvis (hereinafter referred to as a pelvic angle of inclination), which allows the pelvic belts 51a, 51b to be fitted around the lumbar so as to surround the pelvis.

Next, a fitting procedure of the lumbar supporter 10 will be described. First, the lumbar fixed belt 2 and the pelvic fixed belt 5 are unfolded to be in a state in FIGS. 2 or 3, and in this state, the back support portion 21 of the lumbar fixed belt 2 is placed on the substantial center of the lumbodorsal region, and both ends of the belt are held by hands and pulled toward the lumboabdominal side.

At this time, the stretchable portions 22a, 22b are slightly stretched, and the belt portion 23b is placed on the lumboabdominal side, then the hook fastener 42 of the belt portion 23a is placed on the loop fastener 41 of the belt portion 23b to cause engagement between the belt portions 23a and 23b, and thus the lumbar fixed belt 2 is fitted to the human body H.

The fitted lumbar fixed belt 2 can appropriately press the abdomen using a wide shape thereof and hardness by the reinforcing plates 24a, 24b to increase the intra-abdominal pressure, and stably support lumbar vertebrae or the like.

After the lumbar fixed belt 2 is fitted, the pelvic fixed belt 5 is fitted. The pelvic fixed belt 5 has the center integrally fastened to the back support portion 21 of the lumbar fixed belt 2 as described above. Both ends of the pelvic belts 51a, 51b are held by hands and pulled toward the lumboabdominal region with the stretching portion being stretched, and the loop fastener 52 is engaged with the hook fastener 53, thereby integrally surrounding and holding the pelvis.

Thus, the pelvic fixed belt 5 is previously inclined along the pelvic angle of inclination, and tensile stress after fitted occurs along the pelvic angle of inclination, thereby causing the pelvis to be always held in a stable posture at 20° to 30°, which is the angle of physiological forward inclination, and effectively preventing displacement of the lumbar supporter 10 to an upper trunk.

The two belts of the lumbar fixed belt 2 and the pelvic fixed belt 5 are used to hold the entire lumbar, thus minimizing a gap between the supporter and the surface of the human body, and providing a good fit and a less obtrusive appearance.

Figure 4A:
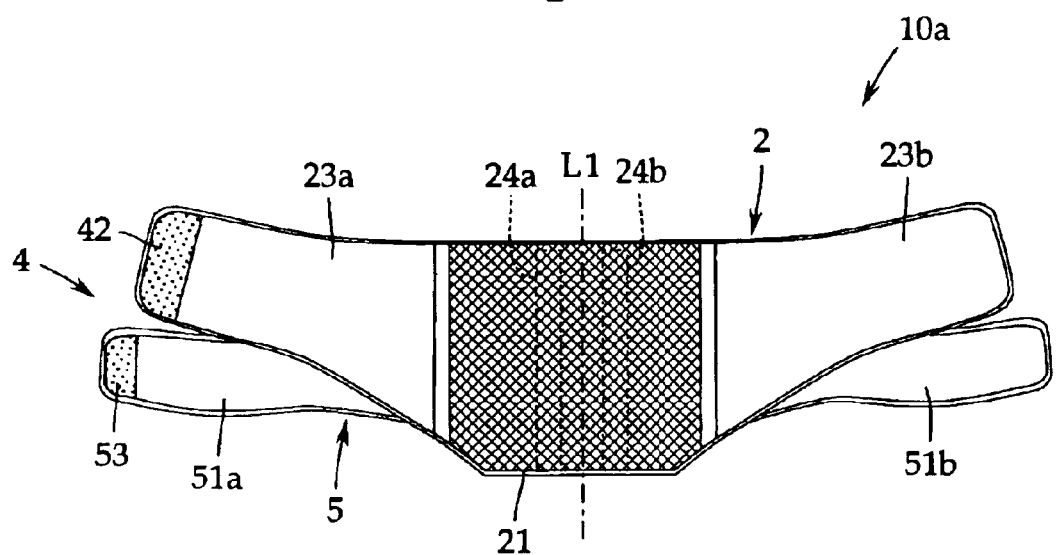
FIG. 4A is a front view of a variation of the lumbar supporter, seen from a lumbodorsal side.
Figure 4B:
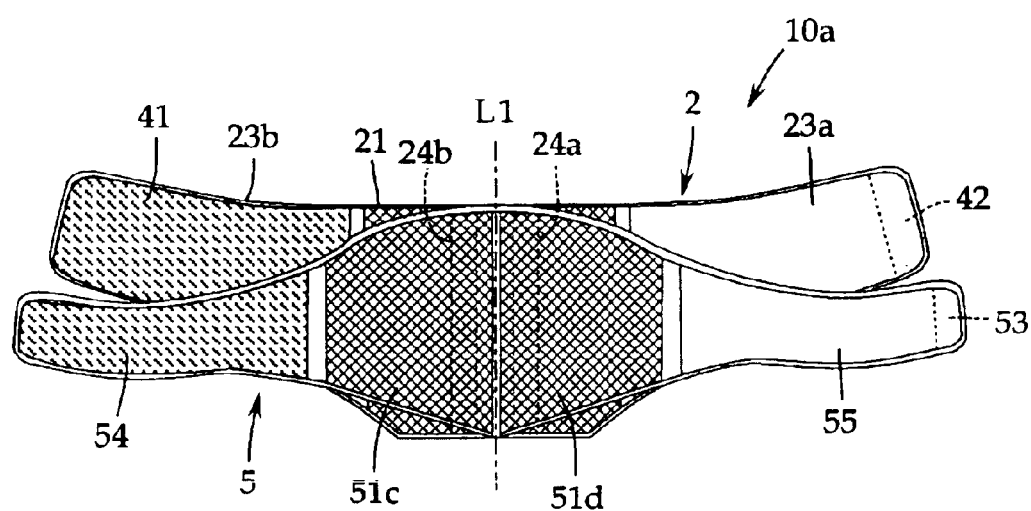
FIG. 4B is a front view of the variation of the lumbar supporter, seen from a lumboabdominal side.

Next, a variation of a lumbar supporter 10a is shown in FIGS. 4A and 4B. The lumbar supporter 10a includes a lumbar fixed belt 2 and a pelvic fixed belt 5, and the pelvic fixed belt 5 is inclined at a predetermined angle along a pelvic angle of inclination, as in the above described embodiment.

In the variation, the lumbar fixed belt 2 has a wide stretchable portion 21 at a center thereof, from both ends of which unstretchable belt portions 23a, 23b extend. In this example, the entire lumbar fixed belt 2 is formed so that a width thereof is gradually reduced from the center toward both ends, and curved so as to easily fit around a trunk of a human body H. The curvature of the curve can be set to any value depending on specifications.

The pelvic fixed belt 5 has wide pelvic belts 51c, 51d at a center thereof, from both ends of which unstretchable belt portions 54, 55 integrally extend, and is curved so that a width thereof is gradually reduced from the center toward tips as in the case of the lumbar fixed belt 2.

In this example, a loop fastener 52 and a hook fastener 53 described in the embodiment are integrally formed on the belt portions 54, 55, and both ends of the pelvic fixed belt 5 can engage each other.

According to the variation, each of the fixed belts 2, 5 is curved to easily fit the surface of the body, and the width thereof is gradually reduced toward the tips, thus even an elderly person with less physical strength can wear the supporter without strain, and further, extended wear of the supporter causes no fatigue. The invention covers such a variation.

The invention has a feature in that the lumbar fixed belt 2 that mainly holds the lumbar and the pelvic fixed belt 5 that mainly holds the pelvis are separately provided, and with this basic configuration, the invention covers variations including changes of materials of the belts or changes of positions. The lumbar fixed belt 2 and the pelvic fixed belt 5 may change places.

The pelvic fixed belt 5 does not require to be sewn together to the lumbar fixed belt 2, and may be removable by a hook-and-loop fastener, or may be inserted into a belt hole or the like formed on the lumbar fixed belt 2. The invention covers such aspects.

The embodiment of the invention has been described in detail, but the scope of the invention according to claims may cover changes, alterations, and equivalents easily achieved by those skilled in the art, who understand the description.

What is claimed is:

1. A lumbar supporter comprising:

a lumbar fixed belt constituted by a band, at least a part of which is stretchable, and fitted from a lumbodorsal region toward a lumboabdominal region of a human body; and a pelvic fixed belt having a center portion overlapping with a center portion of the lumbar fixed belt and sewn together thereat, an upper edge and a lower edge, the upper edge of the pelvic fixed belt being configured to continuously overlap the lumbar fixed belt, the pelvic fixed belt being fitted substantially in parallel along a pelvic angle of inclination of the human body from the lumbodorsal region toward the lumboabdominal region so that the lower edge of the pelvic fixed belt extends below the lumbar fixed belt in a non-overlap relationship with the lumbar fixed belt.

2. The lumbar supporter according to claim 1, wherein an angle of inclination of said pelvic fixed belt is set to 20° to 30° forward toward said lumboabdominal region with respect to a trunk axis as a base axis.

3. The lumbar supporter according to claim 1, wherein said lumbar fixed belt and said pelvic fixed belt are overlapped and sewn together at substantial centers thereof.

4. The lumbar supporter according to claims 1, wherein said lumbar fixed belt has a reinforcing plate placed along said lumbodorsal region.

5. The lumbar supporter according to claim 3, wherein the upper edge of the pelvic fixed belt has portions which are inclined at a predetermined angle with respect to the lower edge.

6. The lumbar supporter according to claim 5, wherein the predetermined angle is about 20° to 30°.

7. The lumbar supporter according to claim 5, wherein the lower edge is essentially straight.

8. The lumbar supporter according to claim 5, wherein said lumbar fixed belt has an upper edge extending substantially linearly.

9. The lumbar supporter according to claim 8, wherein said lumbar fixed belt includes a back support portion with a generally rectangular shape, and belt portions extending laterally outwardly from the back support portion and having a width less than that of the back support portion.

* * * * *